United States Patent [19]

Mendiratta

[11] 4,327,229
[45] Apr. 27, 1982

[54] RECOVERY OF BISPHENOL-A VALUES

[75] Inventor: Ashok K. Mendiratta, Schenectady, N.Y.

[73] Assignee: General Electric Company, Schenectady, N.Y.

[21] Appl. No.: 226,271

[22] Filed: Jan. 19, 1981

[51] Int. Cl.³ .................. C07C 39/16; C07C 37/82
[52] U.S. Cl. .................. 568/728; 568/758; 568/749; 568/759
[58] Field of Search ............ 568/727, 728, 749, 748, 568/758, 759

[56] References Cited

U.S. PATENT DOCUMENTS

| | | | |
|---|---|---|---|
| 2,861,948 | 11/1958 | McKellar | 568/758 |
| 3,049,568 | 8/1962 | Apel | 568/728 |
| 3,172,916 | 3/1965 | Wagner | 568/728 |
| 3,221,061 | 11/1965 | Grover et al. | 568/728 |
| 3,377,369 | 4/1968 | Sargebt et al. | 568/748 |
| 4,107,218 | 8/1978 | Konrad et al. | 560/724 |
| 4,191,843 | 3/1980 | Kwantes et al. | 568/728 |

FOREIGN PATENT DOCUMENTS

| | | | |
|---|---|---|---|
| 1377227 | 12/1974 | United Kingdom | 568/724 |
| 210044 | 1/1968 | U.S.S.R. | 568/724 |

Primary Examiner—Werren B. Lone
Attorney, Agent, or Firm—Joseph T. Cohen; James C. Davis, Jr.

[57] ABSTRACT

An improved process is described for recovery of some of the bisphenol-A values present in the waste streams in an acid-catalyzed bisphenol-A synthesis process.

9 Claims, 1 Drawing Figure

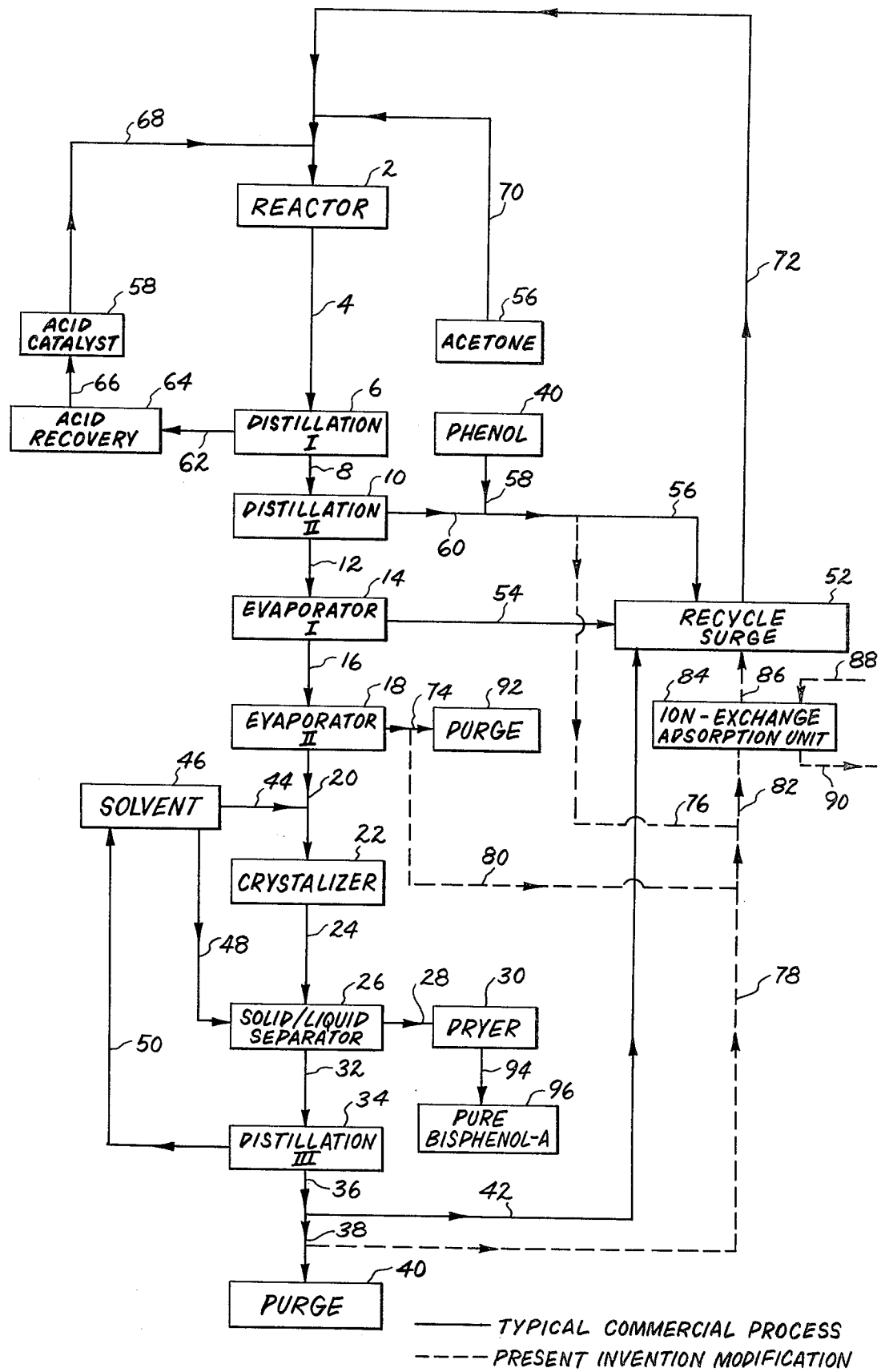

RECOVERY OF BISPHENOL-A VALUES

This invention relates to an improved process for making bisphenol-A, and more particularly, to an improved process for recovering bisphenol-A values in the form of a phenol liquor suitable for recycling in the process for making bisphenol-A.

BACKGROUND OF THE INVENTION

Bisphenol-A, otherwise known as 2,2-bis(4-hydroxyphenyl)propane, is commercially prepared by reacting phenol and acetone in the presence of an acidic catalyst, such as hydrochloric acid, sulfuric acid, or a cation-exchange resin. In one commercial method, acetone is reacted with a stoichiometric excess of phenol in the presence of hydrochloric acid to produce bisphenol-A. The effluent from the reaction contains hydrochloric acid, unreacted phenol, bisphenol-A and the phenol-acetone condensation reaction by-products having color bodies therein. The reaction effluent is passed through a distillation/evaporation system to separate hydrochloric acid, unreacted phenol, lower boiling reaction by-products, crude bisphenol-A, and higher boiling reaction by-products having most of the color bodies therein. The thermal treatment employed in the distillation/evaporation system results in some decomposition/interaction of bisphenol-A and the phenol-acetone condensation reaction by-products, forming more color bodies. The hydrochloric acid, the unreacted phenol and the lower boiling reaction by-products are recycled to the reaction zone and the higher boiling reaction by-products having most of the color bodies therein are purged from the system. The crude bisphenol-A is dissolved in an organic solvent and the high purity bisphenol-A is crystallized from the solution. The crystals are centrifuged, washed with the organic solvent and dried to produce high purity bisphenol-A. The solvent liquor, obtained from the centrifuge, is distilled to produce the organic solvent for recycle and the residual liquor contains the by-products including isomers and color bodies present in the crude bisphenol-A. A part of the residual liquor is purged from the system to maintain the product bisphenol-A quality and to avoid build-up of undesirable by-products in the system, and the balance is recycled to the phenol-acetone condensation reactor. The by-products and the color bodies formed in the phenol-acetone condensation reaction and the distillation/evaporation system are generally defined in the prior art.

The bisphenol-A produced by the above method and separated from the reaction mixture has been effectively removed from the tarry residue by a number of procedures including distillation, crystallization, solvent extraction, spray drying, evaporation, and the like, and combinations thereof. However, it has been calculated that substantial amounts of phenol and re-usable bisphenol-A values can be derived from the tars and liquors derived from the process of making bisphenol-A, and there still remains the need to treat the tars and residues resulting from the initial reaction of the phenol and acetone to recover all possible useful products in order to enhance the value of the bisphenol-A process. Furthermore, it is desirable to remove color bodies and to convert the by-products including isomeric impurities remaining in the residual liquor obtained from crystallizing the crude bisphenol-A with an organic solvent after removal of the organic solvent by distillation. In order to increase the economy of the process of making bisphenol-A in the foregoing reaction and process, in order to reduce the amount of waste resulting from the process, and in order to produce from the waste streams a recycle stream substantially depleted of color bodies, it is desirable to improve the foregoing process of making bisphenol-A from acetone and phenol in the presence of an acid catalyst.

In U.S. Pat. No. 4,107,218, a bisphenol-A recycle stream from the cationic exchange-catalyzed bisphenol-A synthesis process, is decolorized with a cation exchange resin. All or part of the bisphenol-A process mother liquid in this patent is contacted with acidic cation exchange resin to remove color bodies. Phenol is reacted with acetone in a reaction mixture containing a cation exchange catalyst to produce a product mixture containing unconverted reactants, bisphenol-A and phenol-acetone condensation reaction by-products, and the product mixture is separated into bisphenol-A/phenol adduct crystals and a mother liquor stream. The mother liquor stream is recycled to the reaction mixture, and at least a portion of the mother liquor stream is contacted with an acidic cation exchange resin to reduce the content of color bodies contained in the mother liquor recycle stream. In the same patent, there are no tarry residue streams or liquor streams resulting from the distillation of liquors to be treated, only the bisphenol-A/phenol adduct and a mother liquor stream.

SUMMARY OF THE INVENTION

In accordance with the present invention, in the process of making bisphenol-A comprising reacting acetone and phenol in the presence of a mineral acid catalyst to produce a mixture of bisphenol-A and phenol-acetone condensation by-products having color bodies therein, separating the mixture of bisphenol-A and condensation by-products into crude bisphenol-A, lower boiling condensation reaction by-products and higher-boiling condensation by-products having most of the color bodies therein by distillation/evaporation; crystallizing the crude bisphenol-A in the presence of an organic solvent to produce high purity bisphenol-A crystals and a solvent liquor containing phenol-acetone condensation by-products having color bodies therein; separating the high purity bisphenol-A from the solvent liquor; distilling the solvent liquor to produce organic solvent for recycling and residual liquor containing phenol-acetone condensation reaction by-products having color bodies therein including isomeric impurities; purging from the system the higher-boiling condensation reaction by-product (tarry residue stream) and part of the residual liquor to maintain bisphenol-A product color quality and to avoid build-up of by-products in the system; and recycling the balance residual liquor; the improvement comprising (a) adding phenol to part (e.g., up to 50% by weight) of the higher boiling condensation by-products having color bodies therein, and passing the resulting liquor through cation exchange resin to remove color bodies and thereby produce a phenol liquor suitable for recycling; and (b) adding phenol to part of the purged residual liquor, (e.g., up to 75%, by weight) containing phenol-acetone condensation by-products having color bodies therein; and passing the resulting liquor through cation exchange resin to remove color bodies and thereby produce a phenol liquor suitable for recycling.

In one embodiment of the present invention, part of the higher-boiling condensation by-products having color bodies therein, and part of the purged residual liquor containing phenol-acetone condensation by-products having color bodies therein are combined with phenol to form a combined liquor, and the combined liquor is passed through cation exchange resin to remove color bodies and thereby produce a phenol liquor suitable for recycling. In accordance with the present invention, not only is part of the purged residual liquor stream containing phenol-acetone condensation by-products having color bodies therein derived from the crystallization of the crude bisphenol-A with organic solvent purified and depleted of color bodies, but also part of the higher-boiling condensation by-product stream having color bodies therein derived from the tarry residue of the reaction mixture, is substantially depleted of color bodies and converted to a phenol liquor suitable for recycling.

It has also been observed in accordance with the present invention that in addition to decolorization, there is rearrangement of the o,p-isomer of bisphenol-A, that is, 2-(4-hydroxyphenyl)-2-(2-hydroxyphenyl)propane, and some of the other condensation reaction by-products to the p,p-isomer, that is, bisphenol-A.

The present invention is directed only to those processes of making bisphenol-A from the reaction of acetone and phenol in the presence of a mineral acid catalyst in which a tarry residue results from the separation of the ingredients of the reaction mixture by distillation/evaporation, the tarry residue being defined herein as the higher boiling condensation by-products having color bodies therein, as well as a solvent liquor resulting from the crystallization and/or recrystallization of the crude bisphenol-A in the presence of an organic solvent to precipitate out a high purity bisphenol-A. Part of both the tarry residue and the residual liquor derived from the solvent liquor are ultimately passed through cation exchange resin to remove color bodies and thereby produce a phenol liquor suitable for recycling, and in preferred embodiments, a liquor stream derived from the tarry residue and the liquor stream derived from the residual liquor resulting from the crystallization are combined; phenol is added thereto; and the resulting liquor is passed through a cation exchange resin to remove color bodies.

In the practice of the present invention, phenol is added to the separate waste streams and/or to the combined waste streams so that part of the waste streams, that is, the higher-boiling condensation by-product stream having color bodies therein and the residual liquor stream derived from the crystallization or recrystallization step, can be passed through the cation exchange resin at temperatures less than 100° C. and preferably at about 50° C. to 80° C.

For a better understanding of the invention as well as other objects and further features thereof, reference is made to the following detailed description of the invention to be read in connection with the accompanying drawing.

BRIEF DESCRIPTION OF THE DRAWING

The drawing is a schematic flow diagram illustrating a process of making bisphenol-A and one embodiment of the improvement of the present invention.

DETAILED DESCRIPTION OF THE INVENTION

Referring to the drawing which not only embraces one of the preferred embodiments of the improvement of the present invention, but also illustrates one preferred process for the preparation of pure bisphenol-A in order to illustrate the derivation of by-product streams, part of which are converted to a phenol liquor suitable for recycling. An excess of phenol from reservoir 40, acetone from reservoir 56 and mineral acid catalyst, for example, hydrogen chloride, from acid catalyst tank 58, are fed to reactor 2 and heated at a temperature from about 50° C. to 60° C. In reactor 2, which may be a series of reaction vessels, and which may be operated in a batch or a continuous manner, the reaction of phenol with acetone produces bisphenol-A. The effluent or product stream 4 flowing from reactor 2 contains bisphenol-A, unreacted phenol, hydrochloric acid, and a variety of phenol-acetone condensation reaction by-products having color bodies therein and including various isomers, dimers, trimers, and the like well-known in the art. The product stream 4 may be separated by any conventional system so that a stream of crude bisphenol-A and a stream of tarry residue containing higher-boiling condensation by-products having color bodies therein, is separated. In the drawing, the separation step is carried out by distillation columns 6 and 10, and evaporators 14 and 18. Effluent stream 4 passes into distillation column 6 where hydrochloric acid is distilled and recycled to the reactor 2 after passing it through the acid recovery system 64. The distillation column bottom stream 8 goes to the second distillation column 10 where the unreacted phenol is distilled and sent to the recycle surge reservoir 52. The bottom stream 12 from distillation column II 10 goes to evaporator I 14 where lower boiling phenol-acetone reaction by-products and residual phenol are evaporated and recycled to the recycle surge reservoir 52. In evaporator II 18, the residual stream 16 from evaporator II 14 is evaporated to recover crude bisphenol-A stream 20 and high boiling residue stream 74 which is purged from the system in purge 92.

Crude bisphenol-A stream 20 is dissolved in organic solvent 46 and the solution is cooled to crystallize high purity bisphenol-A in crystallizer 22. Typical organic solvents include toluene and methylene chloride for the crystallization of pure bisphenol-A.

The resulting slurry is passed through line 24 to a solid/liquid separation zone comprising a suitable solid/liquid separator 26, equipped with accessories for crystal washing. The crystals, after separation from their mother liquor, are washed with the organic solvent 46 through line 48. The pure crystals are then sent to the dryer 30 through line 28 where the residual organic solvent is removed from the crystals and pure bisphenol-A is recovered at 96. The mother and wash liquors from the separator 26 are obtained in the form of the solvent liquor 32 which contains organic solvent, some bisphenol-A and the various phenol-acetone reaction by-products and impurities present in the crude bisphenol-A stream 20 have color bodies therein. The solvent liquor stream 32 is distilled in distillation III 34 to recover the organic solvent which is recycled to the solvent reservoir 46 through line 50 and the residual liquor stream 36 containing phenol-acetone reaction by-products and impurities having color bodies therein. To maintain color quality of the bisphenol-A and to avoid build-up of phenol-acetone reaction by-products and impurities in the system, a purge stream 38 is withdrawn from the residual liquor stream 36 at 40. The balance of the residual liquor stream 42 is recycled to the recycle surge reservoir 52 through line 42.

In the recycle surge reservoir 52, recycled phenol stream 60, make-up phenol stream 58, lower boiling phenol-acetone reaction by-products stream 54 and the recycled residual liquor stream 42 are mixed and the mixture is sent to the phenol-acetone condensation reactor 2 through line 72.

The modification suggested in the invention consists of mixing part of the recycle phenol stream 76 with part of the purged residual liquor 78 and/or part of the higher boiling tarry residue stream 80 having color bodies therein, and passing this mixture through an ion-exchange adsorption column 84 for the removal of color bodies. A phenol liquor suitable for recycling to the phenol-acetone condensation reactor 2 is removed by stream 86 from ion-exchange adsorption column 84. As indicated above, it has been observed that quantities of the o,p-isomer of bisphenol-A and some other phenol-acetone condensation reaction by-products rearrange to p,p-isomer of bisphenol-A in ion-exchange adsorption column 84.

Although it is not shown in the drawing, an ion-exchange adsorption column may be utilized for removal of the color bodies at any stage in the process where a liquor contains phenol-acetone condensation by-products having color bodies therein. In accordance with the present invention, it is important that a phenol stream be mixed with a tar stream or a liquor stream prior to passing the stream through an ion exchange adsorption column to maintain the stream as a fluid. Since phenol has a melting point of about 41° C., and since the tar streams and liquor streams having melting points in excess of the melting point of phenol, generally at temperatures of about 100° C., the mixed phenol-tar streams and liquor streams can be maintained at about 50° C. to about 80° C., so that the liquors and tars can be conveniently passed through the ion exchange adsorption column or columns and other conduits. In preferred embodiments of the present invention, about 50% to 80% by weight, of molten phenol, based upon the weight of the combined phenol and waste streams, is preferably used. As used herein, the tar stream, tarry residue or heavy ends from the separation step are defined as the higher-boiling condensation reaction by-products having color bodies therein. One skilled in the art can determine the optimum amounts of phenol and optimum temperatures for removing the color bodies from the tarry residues and residual liquors, depending upon the melting points of the tars and the liquors and the constituents of the respective streams.

In accordance with the present invention, one skilled in the art can utilize a single ion exchange adsorption column or multiple ion exchange adsorption columns the latter being preferred so that at least one ion exchange adsorption column can remain on stream while a spent ion exchange adsorption column is being regenerated.

In accordance with the present invention, the ion exchange resin columns may be activated with dry phenol. Further, the ion exchange resin columns having color bodies adsorbed therein may be regenerated by passing a phenol/water mixture therethrough and thereafter passing dry phenol therethrough to obtain an anhydrous resin bed for the next cycle. Phenol/water can be easily reclaimed from the effluent phenol/water wash used in the reactivation procedure by conventional techniques, for example, by distillation.

Although temperatures and flow rates through the bed are not narrowly critical for effective removal of the color bodies, temperature within the range of from about 40° C. to about 150° C., and preferably from about 50° C. to about 80° C., are usually employed. At temperatures below about 40° C. the phenol and other residual constituents may freeze, and at temperatures above about 150° C., the ion-exchange resin may become unstable and/or decomposition or further decomposition or polymerization of bisphenol-A values may occur.

The rate at which the phenol/higher-boiling condensation by-product stream, the phenol/residual liquor stream, and/or the foregoing streams combined, pass through the ion exchange adsorption column are not critical, and optimum flow rates can be easily determined by one skilled in the art. For example, the throughput rate can be up to about 15 ion-exchange resin bed volumes per hour. The preferred throughput rate is from about 1 to about 3 bed volumes per hour.

The cation exchange resin employed in the present invention can be any suitable form including macroreticular cation-exchange resins and microreticular cation-exchange resins. A typical cation exchange resin is a sulfonated polystyrenedivinylbenzene ion-exchange resin. As indicated above, the ion-exchange resins are preferably substantially anhydrous.

The following specific examples describe the process of the present invention. They are intended for illustrative purposes only and should not be construed as a limitation.

A 25 mm diameter glass ion-exchange resin column was used for the following decolorization tests. The column temperature was maintained at 70° C. by circulating hot oil through the column jacket. In the decolorization/reactivation runs, the flow through the column was maintained at 5 mls/minute (downflow) with the help of a metering pump. The reported relative color content in the column feed/effluent is for an absorbance of an ultraviolet wave length at 350 nm calculated on the basis of a concentration of 10 gms of sample in 100 milliliters of methanol. This was done by measuring the absorbance of a 2.5% sample solution (2.5 gms sample diluted with 100 mls methanol) in a 10 cm cell at a wavelength of 350 nm and then multiplying it by 4 to obtain the required absorbance. The feed solution used for decolorization studies was prepared by mixing phenol with isomer (residual liquor) and tar streams (higher-boiling phenol-acetone condensation reaction by-products) from a bisphenol-A manufacturing plant. The isomer stream corresponds to residual liquor effluent stream 38, and the tar stream corresponds to higher-boiling condensation by-products effluent stream 74 in the accompanying drawing.

EXAMPLE 1

The glass ion exchange resin column was charged with 120 mls (45 gms dry resin) of swollen (with 80:20 phenol-water solution) macroreticular, sulfonated polystyrene-divinylbenzene ion-exchange resin beads of 28–48 mesh size supplied commercially by Rohm and Haas Co. under the trademark Amberlyst XN-1010. The resin bed was washed with 4 bed volumes of 80:20 (by weight) phenol-water solution. Initial wash effluent had an absorbance of 1.48. At the end of 4 bed volumes, the absorbance of the effluent was 0.16. This was followed by 3 bed volumes of dry phenol wash to make the bed anhydrous.

A feed solution comprising by weight 80% phenol and 20% isomer stream (residual crystallization liquor) and having an absorbance of 5.20 was contacted with the resin bed. A total of eighteen bed volumes were passed through the column. An overall color reduction of 26% was observed as illustrated in Table 1 below:

TABLE 1

COLOR REDUCTION IN RECRYSTALLIZATION RESIDUAL LIQUOR STREAM

|  | ABSORBANCE |
|---|---|
| Feed | 5.20 |
| Initial effluent (after 2 bed volumes) | 2.75 |
| Intermediate effluent (after 9 bed volumes) | 3.80 |
| Final effluent (after 18 bed volumes) | 4.10 |
| Composite of total effluents | 3.85 |

The data in Table 1 illustrate that the process of the present invention reduces the color bodies of the residual liquor substantially. The effluent, even after 18 bed volumes, shows substantial removal of color bodies.

It was observed that in addition to decolorization, there was some rearrangement of phenol-acetone condensation (reaction) by-products from the o,p-isomer of bisphenol-A to the p,p-isomer of bisphenol-A in the resin bed. Feed and composite effluent had the compositions weight set forth in Table 2 below:

TABLE 2

Rearrangement of Phenol-Acetone Condensation Reaction By-Products in Ion-Exchange Resin Bed

|  | *FEED | EFFLUENT |
|---|---|---|
| Phenol | 80.4 | 79.9 |
| p,p-bisphenol-A | 8.0 | 8.9 |
| o,p-bisphenol-A | 3.2 | 2.9 |
| Other products | 8.4 | 8.3 |

*weight percent in feed or effluent

EXAMPLE 2

A feed solution comprising by weight 80% phenol, 15% isomer stream (crystallization residual liquor) and 5% tar (higher-boiling by-products) stream was prepared from a bisphenol manufacturing process and treated similar to the process of Example 1. This solution had an initial absorbance of 6.25. The resin bed of Example 1 was used for the decolorization studies.

Eighteen bed volumes of waste stream solution having an absorbance of 6.25 were then pumped through the column. An overall color reduction of 29% was observed as illustrated in Table 3 below:

TABLE 3

Color Reduction in Recrystallization Residual Liquor and Higher-Boiling Condensation By-products Streams Combined

|  | ABSORBANCE |
|---|---|
| Feed | 6.25 |
| Initial effluent (after 2 bed volumes) | 3.29 |
| Intermediate effluent (after 9 bed volumes) | 4.40 |
| Final effluent (after 18 bed volumes) | 5.00 |
| Composite of total effluents | 4.42 |

As in Example 1, it was again observed that some rearrangement of the by-product had also taken place. The used resin bed was washed with 4 bed volumes of 80:20, by weight, phenol-water solution to desorb the color bodies. The absorbance of total combined wash effluent was 12.33. This was followed by washing the resin with 3 bed volumes of dry phenol to make the resin bed anhydrous for the next cycle.

In the next cycle, again eighteen bed volumes of feed solution were pumped through the reactivated bed. An overall color reduction of 28% was observed as illustrated in Table 4 below:

TABLE 4

Color Reduction of Feed Solution Identical to Feed Solution of Table 3 In Regenerated Resin Bed

|  | Absorbance |
|---|---|
| Feed | 6.25 |
| Initial effluent (after 2 bed volumes) | 3.32 |
| Intermediate effluent (after 9 bed volumes) | 4.52 |
| Final Effluent (after 18 bed volumes) | 5.00 |
| Composite of total effluents | 4.49 |

The used resin bed was again reactivated as described earlier by washing with phenol-water followed by dry phenol. The total combined wash effluent (from phenol-water wash) hasd an absorbance of 14.48 indicating removal of color bodies from the bed.

Feed solution was again passed through the reactivated bed. The absorbance of effluent after 2 bed volumes was 3.53.

The data of Tables 3 and 4 illustrate that the process of the present invention substantially reduces the color bodies of both residual liquor and higher-boiling condensation by-product streams combined.

EXAMPLE 3

In this example, a microreticular cation exchange resin supplied commercially by Rohm and Haas Co. under the trademark, Amberlite-118, was used for decolorization of waste streams. The feed solution used and the procedures followed for resin loading, wash, adsorption cycle and reactivation were the same as described in Example 2. An overall color reduction of 23% was observed in the first cycle shown in Table 5 below:

TABLE 5

Color Reduction of Recrystallization Residual Liquor and Higher-Boiling Condensation By-Product Effluent Combined

|  | ABSORBANCE |
|---|---|
| Feed | 6.25 |
| Initial effluent (after 2 bed volumes) | 3.13 |
| Intermediate effluent (after 18 bed volumes) | 4.78 |
| Final effluent (after 18 bed volumes) | 5.15 |
| Composite of total effluents | 4.81 |

The saturated bed from the foregoing first cycle was reactivated and was used for the second cycle. A reduction in color content of waste stream solution of 24% was observed in the second cycle as shown in Table 6 below:

TABLE 6

Color Reduction of Feed Solution In Regenerated Resin Bed of Table 5

|  | ABSORBANCE |
|---|---|
| Feed | 6.25 |
| Initial effluent (after 2 bed volumes) | 3.11 |
| Intermediate effluent (after 9 bed volumes) | 4.74 |
| Final effluent (after 18 bed volumes) | 5.18 |
| Composite of total effluents | 4.75 |

As in Examples 1 and 2, rearrangement of reaction by-products was observed when the waste stream solution was contacted with the resin bed. The data in Tables 5 and 6 illustrate that microreticular cation exchange resins also substantially reduce the color bodies in combined effluents from bisphenol-A manufacturing processes.

As seen from the data in the foregoing examples, the phenol liquor suitable for recycling contains a substantial amount of phenol, the p,p-bisphenol-A isomer, the o,p-bisphenol-A isomer and other products. Since bisphenol-A is used in making polycarbonate resins by reaction of the bisphenol-A with phosgene, diphenyl carbonate, and the like, or for making epoxy resins, both resins being used extensively in commercial applications involving moulding, casting, and sheet-forming purposes, it is highly important that the monomeric bisphenol-A used to make such resins be as pure as possible in order to avoid adverse effects on the properties of the polymers thus obtained. The improved process of making bisphenol-A in accordance with the present invention combines at least part of the two waste effluent streams from the manufacturing process and converts them into bisphenol-A values suitable for recycling to the reactor for making bisphenol-A. Thus, additional bisphenol-A values of sufficient purity are returned to the process by the present invention.

While the invention has been described with respect to preferred embodiments, it will be apparent that certain modifications and changes can be made without departing from the spirit and scope of the invention and therefore, it is intended that the foregoing disclosure be limited only by the claims appended hereto.

What we claim as new and desire to secure by Letters Patent of the United States is:

1. In the process of making bisphenol-A comprising reacting acetone and phenol in the presence of mineral acid catalyst to produce a mixture of bisphenol-A, and phenol-acetone condensation by-products having color bodies therein, separating the mixture of bisphenol-A and condensation by-products into crude bisphenol-A, lower boiling condensation reaction by-products and higher-boiling condensation by-products having most of the color bodies therein by distillation/evaporation; crystallizing the crude bisphenol-A in the presence of an organic solvent to produce high purity bisphenol-A and a solvent liquor containing phenol-acetone condensation by-products having color bodies therein; separating the high purity bisphenol-A from the solvent liquor; distilling the solvent liquor to produce organic solvent for recycling and residual liquor containing phenol-acetone condensation reaction by-products having color bodies therein including isomeric impurities, purging from the system the higher-boiling condensation reaction by-products and part of the residual liquor, to maintain bisphenol-A product, color quality and to avoid build-up of by-products in the system; and recycling the balance of residual liquor; the improvement comprising:
    (a) adding phenol to part (e.g., up to 50%) of the higher-boiling condensation by-products having color bodies therein obtained from the separation of the mixture of the bisphenol-A and condensation by-products by distillation/evaporation into crude bisphenol-A, lower boiling condensation reaction by-products and a tarry residue containing higher-boiling condensation by-products having color bodies therein, and passing the resulting liquor through cation exchange resin to remove color bodies and thereby produce a phenol liquor suitable for recycling; and
    (b) adding phenol to part of the purged residual liquor, (e.g., up to 75%) containing phenol-acetone condensation by-products having color bodies therein obtained from the purge stream of higher-boiling condensation reaction by-products and residual liquor after distilling the solvent liquor to produce organic solvent for recycling; and passing the resulting liquor through cation exchange resin to remove color bodies and thereby produce a phenol liquor suitable for recycling.

2. The process of claim 1, further comprising (c) combining the phenol liquor of steps (a) and (b) and passing the combined phenol liquors through cation exchange resin to remove additional color bodies and thereby produce a phenol liquor substantially depleted of color bodies.

3. The process of claim 1, comprising adding about 50% to 80%, by weight, phenol to the higher boiling condensation by-products having color bodies therein.

4. The process of claim 1, further comprising activating the cation exchange resin with dry phenol.

5. The process of claim 1, further comprising regenerating cation exchange resin having color bodies absorbed therein by passing a phenol/water mixture therethrough and thereafter passing dry phenol therethrough.

6. The process of claim 2, comprising combining the higher-boiling condensation by-products having color bodies therein and the residual liquor containing phenol-acetone condensation by-products having color bodies therein with about 50% to 80%, by weight, phenol, based upon the weight of the combined liquors.

7. The process of claim 2, further comprising passing any of the liquor streams through cation exchange resin prior to combining the streams in step (a).

8. The process of claim 2, further comprising activating the cation exchange resin with dry phenol.

9. The process of claim 2, further comprising regenerating cation exchange resin having color bodies absorbed therein by passing a phenol/water mixture therethrough and thereafter passing dry phenol therethrough.

* * * * *